United States Patent [19]

Sabatano

[11] 4,192,299
[45] Mar. 11, 1980

[54] BANDAGE THAT CONTAINS ANTISEPTIC
[76] Inventor: Frank Sabatano, 1726 Colden Ave., Bronx, N.Y. 10462
[21] Appl. No.: 936,716
[22] Filed: Aug. 25, 1978
[51] Int. Cl.² ............................. A61F 13/00; A61F 7/02
[52] U.S. Cl. ........................................ 128/155; 128/268
[58] Field of Search ............... 128/155, 157, 260, 268
[56] References Cited
U.S. PATENT DOCUMENTS

| | | | |
|---|---|---|---|
| 2,595,606 | 5/1952 | Pohjola | 128/268 |
| 2,714,382 | 8/1955 | Alcala | 128/268 |
| 3,297,032 | 1/1967 | Antonik | 128/268 |
| 3,306,292 | 2/1967 | Spees | 128/268 |
| 3,565,075 | 2/1971 | Jerry | 128/268 |

*Primary Examiner*—John D. Yasko
*Attorney, Agent, or Firm*—Richard L. Miller

[57] ABSTRACT

A bandage for dressing a body wound, the bandage including a strip of tape having adhesive on one side thereof, a gauze pad adhered at its center, a foil envelop adhered at one end and containing antiseptic medication, the end of the envelop overlapping on top of the pad and being adhered to one end of a folded over, auxillary, second adhesive tape that covers when the auxillary second tape is pulled off the foil on the tape end causes the medication to automatically squeeze out upon the pad so to be instantly prepared for placing against the wound.

2 Claims, 8 Drawing Figures

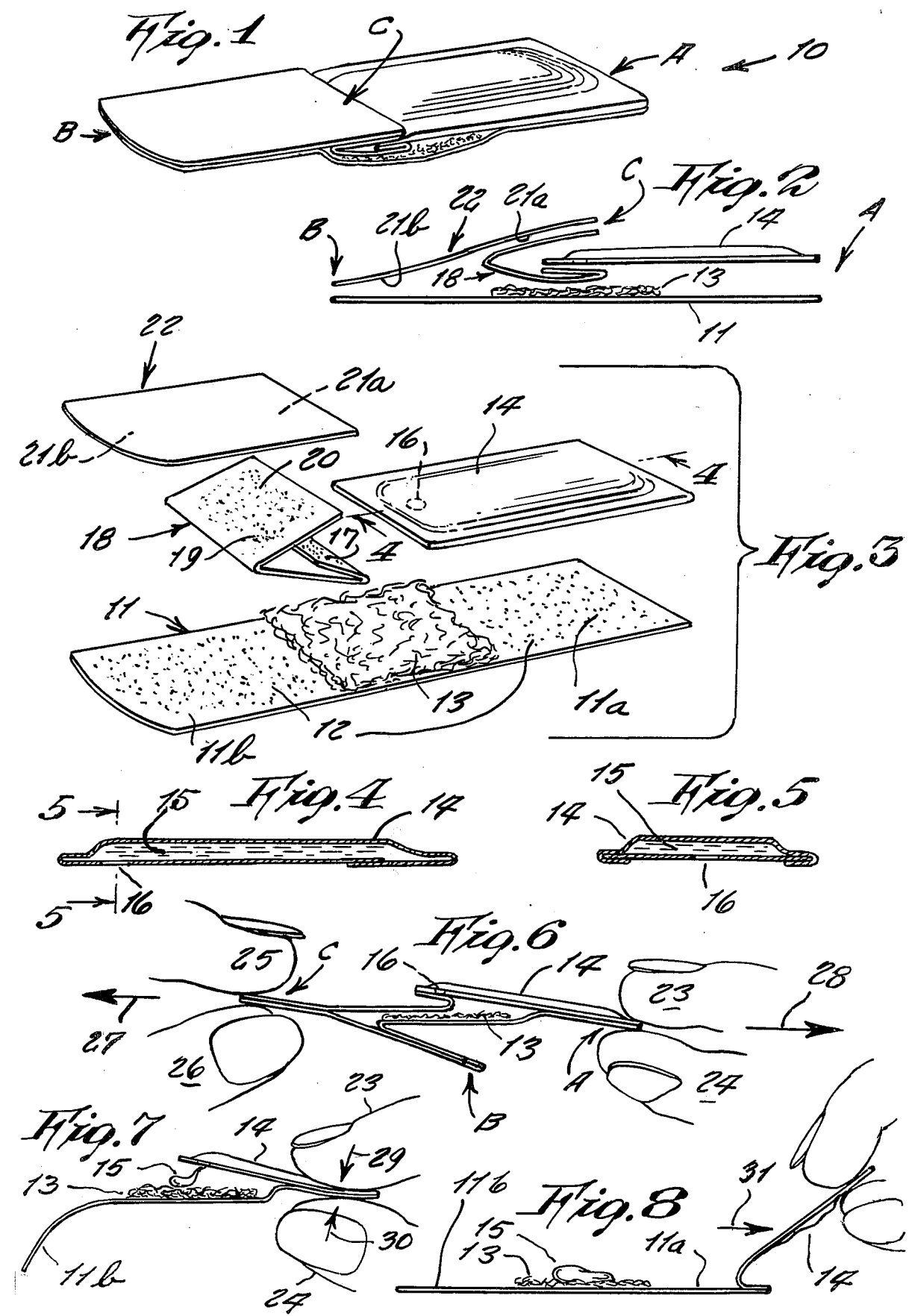

BANDAGE THAT CONTAINS ANTISEPTIC

This invention relates generally to first aid bandages.

A principal object of the present invention is to provide a bandage which is automatically prepared with a medication dressing being dispensed upon a guaze pad thereof at such time when the bandage is being uncovered from its protective covering, for use.

Another object accordingly is to provide a bandage which eliminates the additional chore of manually placing medication on the bandage pad after the bandage has been uncovered from its protective covering.

Still another object is to provide a bandage which accordingly eliminates the need of separately handling bandages and medications at a time when there is an urgency to quickly cover a wound, and particularyl when a person is treating himself without assistance of others.

Yet a further object is to provide a bandage which requires no additional extra manipulation of a person's fingers to get the medication on the bandage; but wherein the medicated pad is instantly accomplished by simply uncovering a bandage from its conventional protective covering similarly to an ordinary "band aid".

Yet a further object is to provide a bandage which would be ideal for use by campers, picnicers, hikers, boat enthusiasts and others when away from home in the out-of-doors, and which eliminates need to carry extra antiseptic in a first aid kit.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

FIG. 1 is a perspective view of the invention.

FIG. 2 is a diagrammatic side edge view thereof, shown with components spaced from each other for easy identification thereof.

FIG. 3 is an exploded perspective view of the components.

FIG. 4 is an enlarged cross sectional view on line 4—4 of FIG. 3.

FIG. 5 is a cross sectional view on line 5—5 of FIG. 4.

FIGS. 6, 7, and 8 show side views of successive steps in opening the bandage and afflication of the medication on the pad thereof, so to be ready for placing upon a wound.

Referring now to the drawings in greater detail, the reference numeral 10 represents a bandage according to the present invention, and which is of the type generally known as "band aids" wherein a bandage is already cut to a size for ready use, includes a central pad for compressing against a wound and has adhensive surface at each end for adhereing to a person's skin. A bandage, thus manufactured, would be retailed in a sterile envelop that can be readily torn off when the bandages is to be used.

In the present invention, the bandage 10 included a long plastic tape 11 having pressure sensitive adhensive 12 on one side. A gauze pad 13 is adhered upon a center thereof. A envelop 14 made of alumimun foil or squeezable plastic is removably adhered upon one end 11a of the tape, the envelop extending part way on top of the pad. The envelop contains an antiseptic jelly 15. An outlet opening 16 on the underside of the envelop is positioned over the pad, and the opening is sealed by a folded over end panel 17 of an auxillary tape 18 having pressure sensitive adhensive 19 on opposite end panels 17 and 20 thereof so as to removably adhere to the envelop and also to one end 21a of a cover 22 made of plastisized paper. The cover also removably adhere at its opposite end 21b to an opposite end 11b of the tape 11.

The bandage thus manufactured, is enclosed inside a sterile envelop (not shown) similarly to a conventional "band aid", and which is torn open when a bandage is needed by a user to dress a wound. After removal from the enclosing envelop, the bandage is as shown in FIG. 1.

To apply the bandage, the user grasps the bandage end A between fingers 23 and 24 of one hand, while with the other hand fingers 25 and 26 he grasps a tab end C (formed by the end of the cover that is attached to panel 20) and pulls the same in a direction away from end A so as to cause the bandage end B to swing or pivot inwardly, as shown in FIG. 6. He then continues to pull the tab end C and the end A apart, (as shown by arrows 27 and 28) so to cause the panel 17 to be pulled off the underside of the envelop 14 and thus expose the outlet opening 16. Due to the fingers 23 and 24 grasping the envelop 14 therebetween, and squeezed as shown by arrows 29 and 30, the antiseptic jelly 15 is thus forcibly squeezed out of the outlet opening 16 so to be discharged directly upon the pad 13, as indicated in FIG. 7. As also shown in FIG. 7, the continued pulling apart of the bandage end A and tab C has caused the panel 17 to be pulled completely off the envelop and a further pulling causes the cover and the auxillary tape to be both pulled completely off the remainder of the bandage so to be discarded. Thus the adhesive on tape end 11b is exposed in order that it may be adhered to the skin of a person as the pad 13 is drawn on top of a wound. Now the opposite end of the deflated envelop 14 is grasped between the fingers and is pulled as shown by arrow 31 so as to cause the envelop to be peeled off and discardrd, thus leaving the adhesive on tape end 11a to be exposed, inorder that it may be adhered to the skin of a person on an opposite side of the wound.

Thus a bandage with antiseptic ointment is easily and quickly applied on a wound.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

I claim:

1. A bandage, comprising in combination an elongated first tape having adhesive upon one side thereof, a gauze pad adhered upon a center thereof, an envelop containing antiseptic medication being adhered upon a first end of said tape, said envelop overlapping upon said pad and having a dispensing outlet in an underside thereof for discharging said medication upon said pad wherein an auxillary, second tape is adhered at one end on an underside of said envelop to seal said outlet, an opposite end of said second tape being adhered to a first end of a cover which at its opposite end is adhered upon a second end of the first said tape.

2. The combination as set forth in claim 1 wherein said opposite end of said second tape and said first end of said tab together form a pull tab for pulling said cover and second tape off said envelop and the first said tape.

* * * * *